US008116852B2

(12) United States Patent
Baker, Jr. et al.

(10) Patent No.: US 8,116,852 B2
(45) Date of Patent: Feb. 14, 2012

(54) SYSTEM AND METHOD FOR DETECTION OF SKIN WOUNDS AND COMPARTMENT SYNDROMES

(75) Inventors: Clark R. Baker, Jr., Newman, CA (US); Shannon E. Campbell, Oakland, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 831 days.

(21) Appl. No.: 11/541,010

(22) Filed: Sep. 29, 2006

(65) Prior Publication Data

US 2008/0146906 A1    Jun. 19, 2008

(51) Int. Cl.
*A61B 6/00*    (2006.01)
(52) U.S. Cl. ......... 600/476; 600/300; 600/306; 600/310
(58) Field of Classification Search .................. 600/310, 600/306, 476, 412, 424, 474, 538, 561, 300, 600/323, 475, 477
See application file for complete search history.

(56) References Cited

U.S. PATENT DOCUMENTS

| | | | |
|---|---|---|---|
| 3,998,550 A | 12/1976 | Konishi et al. | |
| 4,066,068 A | 1/1978 | Nilsson et al. | |
| 4,364,008 A | 12/1982 | Jacques | |
| 4,711,244 A | 12/1987 | Kuzara | |
| 4,723,554 A | 2/1988 | Oman et al. | |
| 4,805,623 A | 2/1989 | Jobsis | |
| 4,850,365 A | 7/1989 | Rosenthal | |
| 4,860,753 A | 8/1989 | Amerena | |
| 4,883,055 A | 11/1989 | Merrick | |
| 4,907,594 A | 3/1990 | Muz | |
| 5,057,695 A | 10/1991 | Hirao et al. | |
| 5,086,781 A | 2/1992 | Bookspan | |
| 5,111,817 A | 5/1992 | Clark et al. | |
| 5,146,091 A | 9/1992 | Knudson | |
| 5,224,478 A | 7/1993 | Sakai et al. | |
| 5,261,405 A * | 11/1993 | Fossel | 600/410 |
| 5,277,181 A | 1/1994 | Mendelson et al. | |
| 5,279,295 A | 1/1994 | Martens et al. | |
| 5,282,467 A | 2/1994 | Piantadosi et al. | |
| 5,337,745 A | 8/1994 | Benaron | |
| 5,337,937 A | 8/1994 | Remiszewski et al. | |
| 5,348,004 A | 9/1994 | Hollub | |
| 5,355,880 A | 10/1994 | Thomas et al. | |
| 5,377,674 A | 1/1995 | Kuestner | |
| 5,499,627 A | 3/1996 | Steuer et al. | |
| 5,564,435 A | 10/1996 | Steinberg | |
| 5,615,689 A | 4/1997 | Kotler | |

(Continued)

FOREIGN PATENT DOCUMENTS

EP    1184663 A2    3/2002
(Continued)

OTHER PUBLICATIONS

Buijs, K., et al., "Near-Infrared Studies of the Structure of Water. I. Pure Water," *The Journal of Chemical Physics*, vol. 39, No. 8, pp. 2035-2041 (Oct. 15, 1963).

(Continued)

*Primary Examiner* — Brian Casler
*Assistant Examiner* — Daniel Huntley
(74) *Attorney, Agent, or Firm* — Fletcher Yoder (57) ABSTRACT

A system configured to provide feedback regarding fluid parameters in the skin and/or compartments of an individual to facilitate early diagnosis of skin wounds and compartment syndromes.

31 Claims, 4 Drawing Sheets

U.S. PATENT DOCUMENTS

| | | | |
|---|---|---|---|
| 5,687,721 A | 11/1997 | Kuhls | |
| 5,701,902 A | 12/1997 | Vari et al. | |
| 5,720,284 A | 2/1998 | Aoyagi et al. | |
| 5,735,284 A | 4/1998 | Tsoglin et al. | |
| 5,747,789 A | 5/1998 | Godik | |
| 5,755,672 A | 5/1998 | Arai et al. | |
| 5,788,643 A | 8/1998 | Feldman | |
| 5,803,908 A | 9/1998 | Steuer et al. | |
| 5,827,181 A | 10/1998 | Dias et al. | |
| 5,833,602 A | 11/1998 | Osemwota | |
| 5,842,981 A | 12/1998 | Larsen et al. | |
| 5,853,364 A | 12/1998 | Baker, Jr. et al. | |
| 5,860,919 A | 1/1999 | Kiani-Azarbayjany et al. | |
| 5,906,582 A | 5/1999 | Kondo et al. | |
| 5,987,351 A | 11/1999 | Chance | |
| 6,064,898 A | 5/2000 | Aldrich | |
| 6,125,297 A | 9/2000 | Siconolfi | |
| 6,149,591 A | 11/2000 | Henderson et al. | |
| 6,163,715 A | 12/2000 | Larsen et al. | |
| 6,178,342 B1 | 1/2001 | Thompson et al. | |
| 6,222,189 B1 | 4/2001 | Misner et al. | |
| 6,240,306 B1 * | 5/2001 | Rohrscheib et al. | 600/316 |
| 6,246,894 B1 | 6/2001 | Steuer et al. | |
| 6,246,898 B1 * | 6/2001 | Vesely et al. | 600/424 |
| 6,263,223 B1 * | 7/2001 | Shepherd et al. | 600/340 |
| 6,280,396 B1 | 8/2001 | Clark et al. | |
| 6,336,044 B1 | 1/2002 | Ghiassi et al. | |
| 6,370,426 B1 | 4/2002 | Campbell et al. | |
| 6,400,971 B1 | 6/2002 | Finarov et al. | |
| 6,402,690 B1 | 6/2002 | Rhee et al. | |
| 6,442,408 B1 * | 8/2002 | Wenzel et al. | 600/310 |
| 6,466,807 B1 | 10/2002 | Dobson et al. | |
| 6,488,677 B1 | 12/2002 | Bowman et al. | |
| 6,512,936 B1 | 1/2003 | Monfre et al. | |
| 6,524,250 B1 * | 2/2003 | Weber et al. | 600/439 |
| 6,526,301 B2 | 2/2003 | Larsen et al. | |
| 6,584,403 B2 * | 6/2003 | Bunn | 701/213 |
| 6,591,122 B2 | 7/2003 | Schmitt | |
| 6,592,574 B1 | 7/2003 | Shimmick et al. | |
| 6,600,946 B1 | 7/2003 | Rice | |
| 6,606,509 B2 | 8/2003 | Schmitt | |
| 6,615,064 B1 | 9/2003 | Aldrich | |
| 6,618,614 B1 | 9/2003 | Chance | |
| 6,635,491 B1 | 10/2003 | Khalil et al. | |
| 6,636,759 B2 | 10/2003 | Robinson | |
| 6,643,543 B2 | 11/2003 | Takehara et al. | |
| 6,654,620 B2 | 11/2003 | Wu et al. | |
| 6,659,967 B1 | 12/2003 | Steinberg | |
| 6,668,181 B2 | 12/2003 | Wenzel et al. | |
| 6,675,029 B2 | 1/2004 | Monfre et al. | |
| 6,687,519 B2 | 2/2004 | Steuer et al. | |
| 6,777,240 B2 | 8/2004 | Hazen et al. | |
| 6,819,950 B2 | 11/2004 | Mills | |
| 6,823,211 B2 * | 11/2004 | Simpson et al. | 600/546 |
| 6,849,046 B1 | 2/2005 | Eyal-Bickels | |
| 6,873,865 B2 | 3/2005 | Steuer et al. | |
| 6,950,699 B1 | 9/2005 | Manwaring et al. | |
| 7,222,624 B2 | 5/2007 | Rashad et al. | |
| 7,257,433 B2 | 8/2007 | Takamura et al. | |
| 7,283,242 B2 | 10/2007 | Thornton | |
| 7,343,186 B2 | 3/2008 | Lamego et al. | |
| 7,740,588 B1 * | 6/2010 | Sciarra | 600/484 |
| 2001/0020122 A1 | 9/2001 | Steuer et al. | |
| 2003/0060693 A1 | 3/2003 | Monfre et al. | |
| 2004/0054290 A1 | 3/2004 | Chance | |
| 2004/0054303 A1 * | 3/2004 | Taylor | 600/587 |
| 2004/0116834 A1 | 6/2004 | Steinberg | |
| 2004/0127777 A1 | 7/2004 | Richti et al. | |
| 2004/0147034 A1 | 7/2004 | Gore et al. | |
| 2004/0230106 A1 * | 11/2004 | Schmitt et al. | 600/310 |
| 2005/0065415 A1 | 3/2005 | Cho et al. | |
| 2005/0113721 A1 * | 5/2005 | Reed et al. | 600/595 |
| 2005/0119538 A1 | 6/2005 | Jeon et al. | |
| 2005/0177046 A1 | 8/2005 | Mills | |
| 2005/0192493 A1 | 9/2005 | Wuori | |
| 2005/0261568 A1 * | 11/2005 | Hular et al. | 600/407 |
| 2005/0268624 A1 * | 12/2005 | Voglewede et al. | 62/126 |
| 2006/0020181 A1 | 1/2006 | Schmitt | |
| 2006/0052680 A1 | 3/2006 | Diab | |
| 2006/0084864 A1 | 4/2006 | Schmitt et al. | |
| 2006/0122475 A1 | 6/2006 | Balberg et al. | |
| 2006/0167350 A1 | 7/2006 | Monfre et al. | |
| 2006/0247506 A1 | 11/2006 | Balberg et al. | |
| 2007/0032707 A1 | 2/2007 | Coakley et al. | |
| 2007/0032709 A1 | 2/2007 | Coakley et al. | |
| 2007/0032710 A1 | 2/2007 | Raridan et al. | |
| 2007/0032711 A1 | 2/2007 | Coakley et al. | |
| 2007/0032712 A1 | 2/2007 | Raridan et al. | |
| 2007/0032713 A1 | 2/2007 | Eghbal et al. | |
| 2007/0032716 A1 | 2/2007 | Raridan et al. | |
| 2007/0073122 A1 | 3/2007 | Hoarau | |
| 2007/0073123 A1 | 3/2007 | Raridan, Jr. | |
| 2007/0073125 A1 | 3/2007 | Hoarau et al. | |
| 2007/0073126 A1 | 3/2007 | Raridan | |
| 2007/0073128 A1 | 3/2007 | Hoarau et al. | |
| 2008/0154104 A1 | 6/2008 | Lamego et al. | |
| 2008/0198361 A1 | 8/2008 | Kaushal et al. | |

FOREIGN PATENT DOCUMENTS

| | | |
|---|---|---|
| EP | 1491135 | 12/2004 |
| FR | 2710517 | 4/1995 |
| JP | 4-40940 | 2/1992 |
| JP | 05-329163 | 12/1993 |
| JP | 11-244266 | 9/1999 |
| JP | 2004 081427 A | 3/2004 |
| WO | WO 95/19562 A | 7/1995 |
| WO | WO 98/34097 | 8/1998 |
| WO | WO 00/71025 A1 | 11/2000 |
| WO | WO 93/13706 A2 | 1/2001 |
| WO | WO 01/16577 A1 | 3/2001 |
| WO | WO 03/010510 A | 2/2003 |
| WO | WO 2005/041765 A | 5/2005 |
| WO | 2006100685 | 9/2006 |

OTHER PUBLICATIONS

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).

Potts, R.O., et al., "A Noninvasive, in Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).

Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).

Bommannan, D., et al., "Examination of Stratum Corneum Barrier Function in Vivo by Infrared Spectroscopy," *J. Invest Dermatol*, vol. 95, pp. 403-408 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Martin, K., "Direct Measurement of Moisture in Skin by Nir spectroscopy," *J. Soc. Cosmet. Chem.*, 44:249-261 (1993).

Matcher, S. J., et al., "Absolute quantification of deoxyhaemoglobin concentration in tissue near infrared spectroscopy," *Phys. Med. Biol.*, vol. 39, pp. 1295-1312 (1994).

Takeo, T. et al., "Skin Hydration State Estimation Using a Fiber-Optic Refractometer," *Applied Optics*, vol. 33, No. 19, Jul. 1994, p. 4267-4272.

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Kumar, Gitesh, et al., "Non-Invasive Optical Assessment of Tissue Hydration," *International conference on Biomedical Engineering*, Jun. 3-5 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

Martin, Kathleen, "In Vivo Measurements of Water in Skin by Near-Infrared Reflectance," *Applied Spectroscopy*, vol. 52, No. 7, 1998, pp. 1001-1007.

Stranc, M.F., et al., "Assessment of tissue viability using near-infrared spectroscopy," *British Journal of Plastic Surgery*, vol. 51, pp. 210-217, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Fornetti, Willa C., et al., "Reliability and validity of body composition measures in female athletes," Journal of Applied Physiology, vol. 87, pp. 1114-1122, (1999).

Kalantar-Zadeh, Kamyar, et al., "Near infra-red interactance for nutritional assessment of dialysis patients," *Nephrol Dial Transplant*, vol. 14, pp. 169-175 (1999).

Sowa et al., "Near-infrared spectroscopic assessment of tissue hydration following surgery", *Journal of Surgical Research*, 86:62-69 (1999).

Lucassen, G., et al., "Water Content and Water Profiles in Skin Measured by FTIR and Raman Spectroscopy," *Proc. SPIE*, vol. 4162, pp: 39-45 (2000).

Attas, Michael, et al., "Visualization of cutaneous hemoglobin oxygenation and skin hydration using near-infrared spectroscopic imaging," *Skin Research and Technology*, vol. 7, pp. 238-245, (2001).

Du, Y., et al., "Optical properties of porcine skin dermis between 900 nm and 1500 nm," *Phys. Med. Biol.*, vol. 46, pp. 167-181 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Lever, M., et al., "Some ways of looking at compensatory kosmotropes and different water environments," *Comparative Biochemistry and Physiolog.*, vol. 130, Part A, pp. 471-486, (2001).

Sowa et al., "Near infrared spectroscopic assessment of hemodynamic changes in the early post-burn period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Attas, E. Michael, et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).

Bouwstra, Joke A., et al., "Water Distribution and Related Morphology in Human Stratum Corneum at Different Hydration Levels," *J. Invest Dermatol*, vol. 150, pp. 750-758 (2003).

Grandjean et al., "Hydration: issues for the $21^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp.-1471-1477 (2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, ppl 185-190 (Apr. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

Arimoto et al., "Non-contact skin moisture measurement based on near-infrared spectroscopy", *Applied Spectroscopy*, 58(12):1439-1445 (2004).

\* cited by examiner

SYSTEM AND METHOD FOR DETECTION OF SKIN WOUNDS AND COMPARTMENT SYNDROMES

BACKGROUND

1. Field of Invention

The present invention relates generally to medical devices and, more particularly, to devices used for determining physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, caregivers, such as doctors and nurses, desire to discover ailments in a timely manner in order to better care for patients. The unfortunate passage of time prior to discovering an ailment may limit treatment options and, in some instances, may lead to irreversible damage. If an ailment is discovered early enough, however, a variety of remedial options and corrective actions may be initiated in order to treat the condition and prevent further damage to the health of the patient. Accordingly, healthcare professionals are continuously pursuing methods to expedite the diagnosis of a problem or to anticipate a potential problem in order to better serve their patients.

Skin wounds stem from a number of different causes and understanding the etiology of the wounds allows for appropriate treatment. Some major categories for skin wounds include pressure ulcers (a/k/a bed sores), skin tears, venous ulcers, arterial ulcers, diabetic skin ulcers, and melanoma. The localization of fluid in the dermis is a precursor in a variety of skin wounds but is often not detected until signs of edema and the breakdown of skin become visually apparent. At this point, the number of treatment options is limited and initiating treatment generally results in a very slow healing process or a worsening of the condition. Concomitantly, changes in protein content in some pathologies result in increased risk of the development and/or morbidity associated with skin wounds. Epidermal hyper-proliferation and/or dermal fibrosis result in changes in the distensibility of the collagen networks and, therefore, the water holding capability of the tissue. Early detection of skin edema could significantly improve diagnosis and treatment of these morbidities.

The various types of skin wounds can be differentiated by knowing the patient history, as well as if and where the fluid is localizing. As an example, pressure sores are often marked by the presence of hemosiderin deposits (a protein resulting from the breakdown of red blood cells) and fluid accumulation in all layers of the dermis. Venous ulcers have a dramatic increase in fluid primarily in the papillary dermis. Alternatively, skin tears exhibit little change and a net loss of water from the dermis Commonly, pressure sores occur on individuals where pressure is applied due to patient lying down or sitting in a chair and occur most frequently on the back of the head, the shoulders and shoulder blades, the elbows, the tailbone and base of the buttocks, the hips, the knees and sides of legs, and the heel and bony parts of the feet. In severe cases, pressure sores may necessitate amputation. Bed sores, for example, are a type of pressure sore seen in patients who have remained in bed for prolonged periods. Several discrete steps have been observed to be associated with the development of bed sores. Fluid is initially forced away from pressure points and then returns to create an inflammatory response causing redness and pitting. The redness leaves and eventually the skin hardens. Finally, the skin splits and a bed sore is formed. Other types of skin wounds, such as diabetic ulcers and cancer, develop differently and may not exhibit the same characteristics.

Currently, physical examination by the clinician and patient history are primarily used in determining skin wound etiology. To date, however, little work has been done to determine the spectral changes in the skin during skin wound development. In some cases, ultrasound technology is used to determine intradermal echogenicity. However, use of ultrasound technology may have several disadvantages. For example, ultrasound technology may not be sensitive to minor or minute changes, as the ultrasound technology only indicates when macroscopic changes have occurred. Additionally, ultrasound technology is not specific, meaning it may have inter-patient variability.

In addition to the localization of fluid in the dermis, excessive accumulations of fluid can occur in a variety of body compartments. Such accumulations may occur due to injury, inflammation, or excessive fluid resuscitation. In general, these accumulations cause an increase in pressure within the compartment and cut off blood flow, potentially causing organ failure and necrosis. Treatment typically requires incisions to relieve pressure. For example, abdominal compartment syndrome causes organ ischemia and failure, and it is commonly treated by opening the abdomen. Additionally, extremity compartment syndrome may cause ischemia and gangrene, and it is commonly treated by fasciotomies.

The occurrence of extremity compartment syndrome depends primarily on the precipitating injuries. For major fractures with associated vascular injury, prevalence has been estimated at 15-30%. Chronic and acute exertional compartment syndromes are also known. Extremity compartment syndrome is diagnosed by pain, paresthesia, pressure, pallor, paralysis, and pulselessness, in descending order of frequency and includes conditions such as shin splints and gout.

The prevalence of intra-abdominal hypertension (tissue pressure greater than 12 mm of Hg) has been estimated at 2-33% in the critically ill, with about half developing abdominal compartment syndrome (greater than 20 mm of Hg). Diagnosis and treatment of abdominal compartment syndrome currently begins at an intra-abdominal pressure greater than 12 mm Hg (normal is less than 5 mm Hg). Intra-compartmental pressures less than 20 mm Hg are generally considered acceptable only if carefully monitored.

SUMMARY

Certain aspects commensurate in scope with the originally claimed invention are set forth below. It should be understood that these aspects are presented merely to provide the reader with a brief summary of certain forms the invention might take and, these aspects are not intended to limit the scope of the invention. Indeed, the invention may encompass a variety of aspects that may not be set forth below.

In accordance with one aspect of the present invention there is provided a method for determining fluid parameters of living tissue. The method includes transmitting electromagnetic radiation at a tissue site using an emitter and detecting the electromagnetic radiation reflected and scattered by the tissue using a photodetector, the photodetector generating a signal corresponding to the detected electromagnetic radiation. The generated signals are processed to calculate fluid parameters of the tissue site. The method also includes correlating the calculated fluid parameters to a condition status by comparing the calculated fluid parameters with baseline fluid parameters and correlating the comparison to the condition status. The condition status is then indicated on a display.

In accordance with another aspect of the present invention there is provided a system for detecting skin wounds and compartment syndromes. The system includes a sensor comprising at least one emitter and at least one detector and a spectrophotometric unit communicatively coupled to the sensor. The spectrophotometric unit being configured to calculate fluid parameters and correlate the fluid parameters to a condition status, wherein the spectrophotometric unit compares the calculated fluid parameters to baseline fluid parameters and determines the condition status from the comparison. The system also includes a display coupled to the spectrophotometric unit configured to display the condition status.

In accordance with yet another aspect of the present invention there is provided a method for diagnosing skin wounds and compartment syndromes. The method including selecting a baseline fluid parameter of a tissue site in a spectrophotometric device and using the spectrophotometric device to calculate data indicative of a condition status. Using the spectrophotometric device comprises placing a sensor on an area of a patient's skin over the tissue site for which baseline fluid parameters were entered and taking measurements using the sensor, the spectrophotometeric device being configured to display the measurements. The method also includes making a diagnosis based on consideration of the patient's medical history and the data calculated by the spectrophotometric monitor.

BRIEF DESCRIPTION OF THE DRAWINGS

Certain exemplary embodiments are described in the following detailed description and in reference to the drawings, in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The use of spectrophotometric means for measuring and calculating fluid metrics are described in U.S. Pat. No. 6,591, 122. Additionally, U.S. Pub. 2003-0220548, 2004-0230106, 2006-0084864; U.S. Ser. Nos. 11/283,506 and 11/282,947; and the patent application titled "Tissue Hydration Estimation by Spectral Absorption Bandwidth Measurement" U.S. Ser. No. 11/528,154, discuss methods for measuring and calculating fluid metrics. The techniques, methods and apparatuses disclosed in the aforementioned patents, publications and applications may be implemented in particular embodiments of the present invention. As such, each of the aforementioned patents, publications and applications are incorporated herein by reference.

The fluid metrics computed by the above mentioned references typically have correlated a local measurement to a whole body water value. Spectrophotometric means, however, may also be used in calculating a local fluid measurement. Specifically, similar measurements, such as the ratio of water-to-water and other constituents, may be taken but the data may be interpreted to indicate a local fluid metric rather than a whole body fluid metric. The local fluid measurement may then be used in the diagnosis of various skin disorders as well as compartment syndromes, as will be discussed in detail below.

Human organs have a normal water content that may be used as a baseline reference for determining if any irregularities are present The percent water component of most organs is 50-80%, whereas the percent water component of skin is approximately 70% and the water percentage of the lungs is approximately 95%. A local fluid measurement may be compared against the reference level, and deviation from the reference level may be indicative of various conditions that may be present in a particular organ or compartment. In the case of compartmental syndromes, for example, an increase of fluid above the reference level in a particular compartment may be detected by a spectrophotometric monitor. This reference level may be a predetermined patient-independent level or an earlier measurement on the same patient and site, or concurrent measurement from one or more different sites on the same patient.

Figure 1:
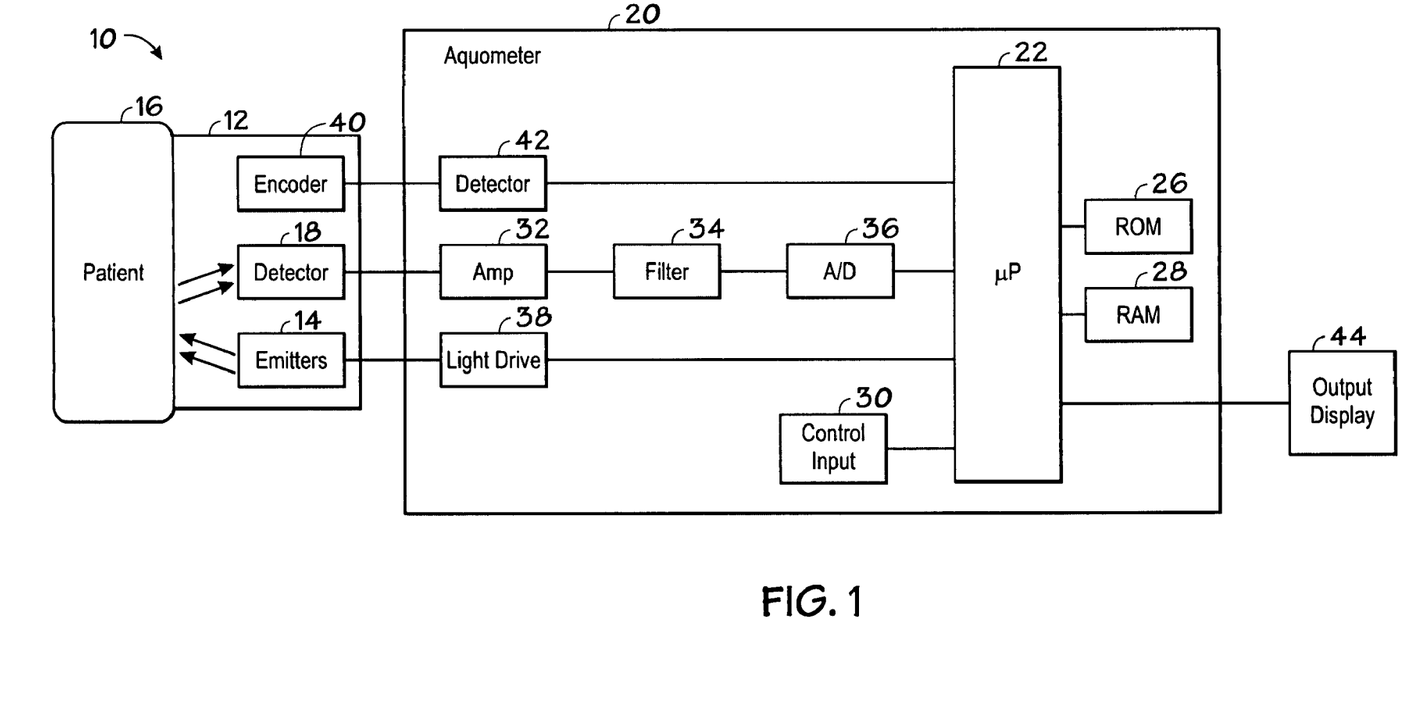
FIG. 1 illustrates a block diagram of a diagnostic system in accordance with an exemplary embodiment of the present invention.

The use of spectrophotometric devices provides the advantage of early detection, allowing for proper treatment and preventative measures to be taken to avoid further damage. Additionally, the spectrophotometric devices are non-invasive. FIG. 1 illustrates a block diagram implementing a spectrophotometric device in a diagnostic system 10 in accordance with an exemplary embodiment of the present invention. The diagnostic system 10 includes a sensor unit 12 having an emitter 14 configured to transmit electromagnetic radiation, such as light, into the tissue of a patient 16. The electromagnetic radiation is scattered and absorbed by the various constituents of the patient's tissues, such as water and protein. A photoelectric detector 18 in the sensor 12 is configured to detect the scattered and reflected light and to generate a corresponding electrical signal. The sensor 12 directs the detected signal from the detector 18 into a spectrophotometric device 20.

The spectrophotometric device 20 has a microprocessor 22 which calculates fluid parameters using algorithms programmed into the spectrophotometric device 20. The microprocessor 22 is connected to other component parts of the spectrophotometric device 20, such as a ROM 26, a RAM 28, and control inputs 30. The ROM 26 holds the algorithms used to compute the fluid levels or metrics. The RAM 28 stores the values detected by the detector 18 for use in the algorithms.

Methods and algorithms for determining fluid parameters are disclosed in U.S. Pub. No. 2004-0230106, which has been incorporated herein by reference. Some fluid parameters that may be calculated include water-to-water and protein, water-to-protein, and water-to-fat. For example, in an exemplary embodiment the water fraction, $f_w$, may be estimated based on the measurement of reflectances, $R(\lambda)$, at three wavelengths ($\lambda_1=1190$ nm, $\lambda_2=1170$ nm and $\lambda_3=1274$ nm) and the empirically chosen calibration constants $c_0$, $c_1$ and $c_2$ according to the equation:

$$f_w = c_2 \log[R(\lambda_1)/R(\lambda_2)] + c_1 \log[R(\lambda_2)/R(\lambda_3)] + c_0. \quad (1)$$

In an alternative exemplary embodiment, the water fraction, $f_w$, may be estimated based on the measurement of reflectances, $R(\lambda)$, at three wavelengths ($\lambda_1=1710$ nm, $\lambda_2=1730$ nm and $\lambda_3=1740$ nm) and the empirically chosen calibration constants $c_0$ and $c_1$ according to the equation:

$$fw = c_1 \frac{\log[R(\lambda_1)/R(\lambda_2)]}{\text{Log}[R(\lambda_3)/R(\lambda_2)]} + c_0. \quad (2)$$

Total tissue water accuracy better than ±0.5% can be achieved using Equation (2), with reflectances measured at the three closely spaced wavelengths. Additional numerical simulations indicate that accurate measurement of the lean tissue water content, $f_w^1$, can be accomplished using Equation (2) by combining reflectance measurements at 1125 nm, 1185 nm and 1250 nm.

In an alternative exemplary embodiment, the water content as a fraction of fat-free or lean tissue content, $f_w^1$, is measured. As discussed above, fat contains very little water so variations in the fractional fat content of the body lead directly to variations in the fractional water content of the body. When averaged across many patients, systemic variations in water content result from the variation in body fat content. In contrast, when fat is excluded from the calculation, the fractional water content in healthy subjects is consistent. Additionally, variations may be further reduced by eliminating the bone mass from the calculations. Therefore, particular embodiments may implement source detector separation (e.g. 1-5 mm), wavelengths of light, and algorithms that relate to a fat-free, bone-free water content.

In an alternative embodiment, the lean water fraction, $f_w^1$, may be determined by a linear combination of two wavelengths in the ranges of 1380-1390 nm and 1660-1680 nm:

$$f_w^1 = c_2 \log[R(\lambda_2)] + c_1 \log[R(\lambda_1)] + c_0. \quad (3)$$

Those skilled in the art will recognize that additional wavelengths may be incorporated into this or other calibration models in order to improve calibration accuracy.

In yet another embodiment, tissue water fraction, $f_w$, is estimated according to the following equation, based on the measurement of reflectances, $R(\lambda)$, at a plurality of wavelengths:

$$fw = \frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}}, \quad (4)$$

where $p_n$ and $q_m$ are calibration coefficients. Equation (4) provides cancellation of scattering variances, especially when the N+1 wavelengths are chosen from within the same band (i.e. 950-1400 nm, 1500-1800 nm, or 2000-2300 nm).

Referring again to FIG. 1, control inputs 30 allow a user to interface with the spectrophotometric monitor 20. For example, if a particular spectrophotometric device 20 is configured to detect compartmental disorders as well as skin disorders, a user may input or select parameters, such as baseline fluid levels for the skin or a particular compartment of the body that is to be measured. Specifically, baseline parameters associated with various compartments or regions of the body or skin may be stored in the spectrophotometric monitor 20 and selected by a user as a reference level for determining the presence of particular condition. Additionally, patient data may be entered, such as weight, age and medical history data, including, for example, whether a patient suffers from emphysema, psoriasis, etc. This information may be used to validate the baseline measurements or to assist in the understanding of anomalous readings. For example, the skin condition psoriasis would alter the baseline reading of skin water and, therefore, would affect any determination of possible bed sores or other skin wounds.

Detected signals are passed from the sensor 12 to the spectrophotometric device 20 for processing. In the spectrophotometric device 20, the signals are amplified and filtered by amplifier 32 and filter 34, respectively, before being converted to digital signals by an analog-to-digital converter 36. The signals may then be used to determine the fluid parameters and/or stored in RAM 28.

A light drive unit 38 in the spectrophotometric device 20 controls the timing of the emitters 14. While the emitters are manufactured to operate at one or more certain wavelengths, variances in the wavelengths actually emitted may occur which may result in inaccurate readings. To help avoid inaccurate readings, an encoder 40 and decoder 42 may be used to calibrate the spectrophotometric monitor 20 to the actual wavelengths being used. The encoder 40 may be a resistor, for example, whose value corresponds to coefficients stored in the spectrophotometric device 20. The coefficients may then be used in the algorithms. Alternatively, the encoder 40 may also be a memory device, such as an EPROM, that stores information, such as the coefficients themselves. Once the coefficients are determined by the spectrophotometric device 20, they are inserted into the algorithms in order to calibrate the diagnostic system 10.

The spectrophotometric device 20 may be configured to display the calculated parameters on display 44. The display 44 may simply show the calculated fluid measurements for a particular region of tissue where the sensor has taken measurements. The fluid measurements may be represented as a ratio or a percentage of the water or other fluid present in the measured region. As the ratio or percentage may not have any particular significance to a caregiver or clinician, the spectrophotometric monitor may be programmed to correlate the ratio or percentage to a number indicative of a risk level or of a potential stage of development of a particular condition. For example, if a normal fluid ratio is measured, a "1" may be outputted on the display 44. Alternatively, if an abnormal, but not severely abnormal fluid ratio is measured, a "2" may be displayed. If a severely abnormal measurement is taken, a "3" may be displayed. A color display may also be programmed to correlate the fluid ratios with a particular color. For example, a green, yellow or red light may be shown on the display corresponding to normal, abnormal, and severely abnormal readings, respectively. The color may be used independently or in combination with the number indicator scheme. Regardless of the manner of presentation, the objective is to present the fluid metric information to a clinician in a manner that may be quickly and easily understood.

In a more complex system, the display 44 may show a graphical image illustrating the fluid measurements or fluid ratios across an area, such as a pressure point and the peripheral area about the pressure point, for example. Regions may be shaded or color coded to indicate relative fluid levels or fluid ratios. For example, normal fluid levels or fluid ratios may be indicated by presenting the region with a green hue on the display 44. Alternatively, regions that may deviate from a normal fluid level or fluid ratio may be indicated by coloring the region a reddish hue, for example. As the fluid level or fluid ratio may change across an area being measured, the differences in the fluid ratio may be shown by the shading or coloring technique. Indeed, a single graphical image may demonstrate a wide range of shades or hues corresponding to the fluid ratio of a particular region. Such an output display would be advantageous in determining exactly what the problem and/or what the etiology might be. Additionally, the graphics may aid in determining the exact location of problem areas, and the severity of the problem.

Figure 2:
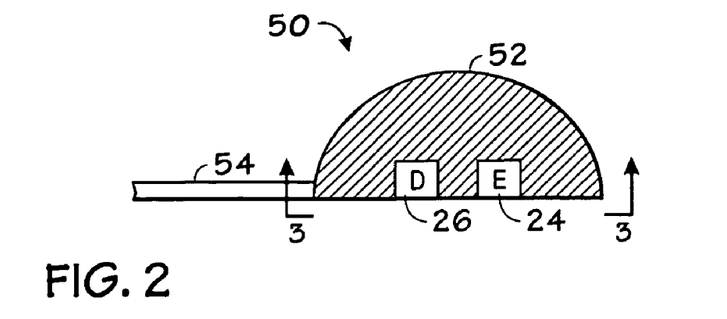
FIG. 2 illustrates a cross-sectional view of a sensor for use with the system of FIG. 1 in accordance with an exemplary embodiment of the present invention.
Figure 3:
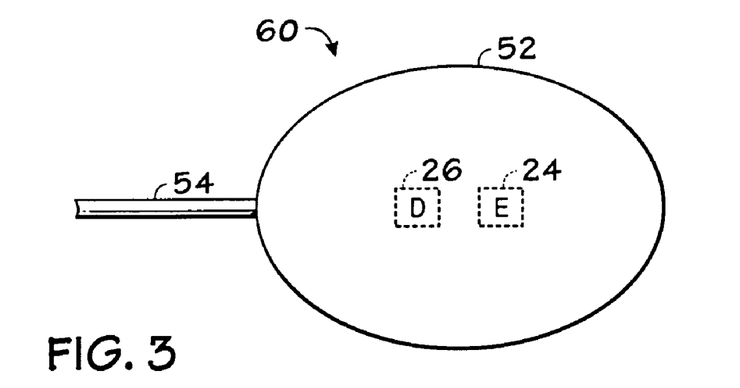
FIG. 3 illustrates an alternative view of the sensor in the plane indicated by lines 3-3 of FIG. 2 in accordance with an exemplary embodiment of the present invention.

Turning to FIGS. 2 and 3, a sensor 50 is illustrated in accordance with an exemplary embodiment of the present invention. Specifically, FIG. 2 illustrates a cross-sectional view of the sensor 50. The sensor 50 may be a handheld sensor that a caregiver can move around on a patient. As can be seen in FIG. 2, the sensor 50 may have a housing 52 having a contoured upper surface to allow a user to easily hold onto the sensor 50. For example, the housing 52 may be similar in size and shape to a computer mouse. The sensor 50 may be communicatively coupled to the spectrophotometric device 20 via a cable 54. Alternative embodiments may employ wireless communication technology to transmit information back to spectrophotometric monitor 20, thus eliminating the cable 54.

An alternative view of the sensor 50, in the plane indicated by the lines 3-3 of FIG. 2, is illustrated in FIG. 3. Specifically, FIG. 3 shows a substantially flat surface of the sensor housing 52. The emitter 24 and detector 26 are located on this surface to allow them to efficiently couple to the patient's skin during use. An optical coupling gel, transparent talc, or other medium may be used to aid in achieving a proper optical coupling between the emitter and detector and the patient's skin.

The spacing between the emitter 24 and detector 26 may be determined based upon the region of skin or compartment of the body that is to be tested. Generally, for relatively shallow probing, the emitter and detector may be relatively close to one another, while for deeper probing the emitter 24 and detector 26 will be further separated. For example, when diagnosing skin wounds, the emitter 24 and detector 26 may be one to five mm apart, because the electromagnetic radiation need only penetrate into layers of skin. However, for detecting compartment syndromes, the emitter 24 and detector 26 may be placed further apart, such as five to 15 mm apart, for example, to allow the electromagnetic radiation to penetrate into deeper tissue before being reflected or scattered to the detector 26. Those skilled in the art will recognize that somewhat shorter and less strongly absorbed wavelengths may be preferred in conjunction with these longer spacings.

Figure 4:
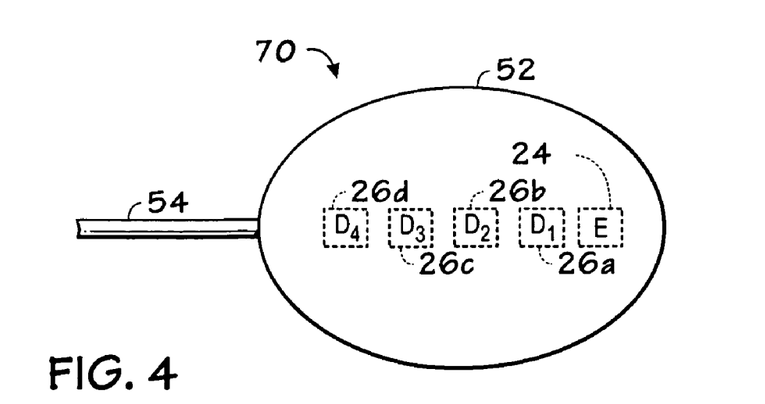
FIG. 4 illustrates a sensor having multiple detectors in accordance with an alternative embodiment of the present invention.

Turning to FIG. 4, a sensor 70 having multiple detectors in accordance with an alternative embodiment of the present invention is illustrated. The sensor 70 is capable of sensing various depths of tissue because of the multiple detectors 26a-d. Any number of detectors 26a-d may be used, and the more detectors that are used, the higher the resolution. In this example, the sensor 70 has four detectors 26a-d arranged linearly with increasing distance from the emitter 24. The detector 26a, in closest proximity to the emitter 24, is used for sensing in shallow tissue, as the light transmitted from the emitter 24 does not penetrate far into the tissue before arriving back at the detector 26a. Alternatively, the detector 26d, furthest away from the emitter 24, may be used for sensing deeper tissue because the signals from emitter 24 penetrate deeper into the tissue before arriving at detector 26d than those that arrive at detector 26a. Accordingly, this arrangement allows for the spectrophotometric device 20 to detect at multiple depths of tissue. Those skilled in the art of mechanical design will recognize that similar results may be achieved with a sensor having a single emitter and detector location with adjustable spacing between them, or a sensor having multiple emitters or emitter locations and a single detector or detector location.

Figure 5:
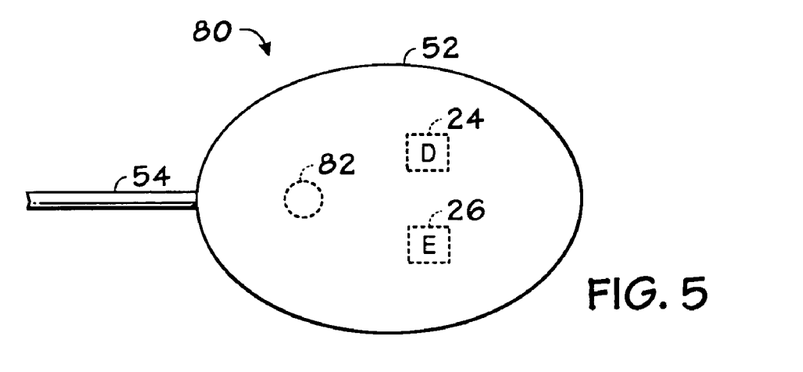
FIG. 5 illustrates a sensor having a roller-ball in accordance with another alternative exemplary embodiment of the present invention.

In order to create a graphical representation of the area tested, a sensor may have a means for indicating a relative position. FIG. 5 illustrates a sensor 80 having a roller-ball 82 in accordance with an exemplary embodiment of the present invention. The roller-ball 82 tracks the movement of the sensor 80 as it is moved across a potential problem area of a patient. The roller-ball 82 correlates the movement of the sensor to a specific location relative to a starting point. The starting point may be determined by actuation of a button on the sensor or monitor or through voice command, for example, when the sensor 80 is initially placed in contact with the patient's skin. Alternatively, the start position may be determined by a using a relative position indicator on a bed or operating table. Measurements are taken as the sensor 80 is moved across a patient's skin. The measurements are then pieced together by correlating the measurements to the specific location relative to the starting point as determined by the roller-ball 82. A graphical representation of the area over which the sensor 80 passes can then be generated. Thus, a caregiver or patient may receive information in a graphical form. The graphical representation may be useful to a caregiver for many reasons. Particularly, the graphics may be useful in determining the exact parameters of the potential skin wound or compartment syndrome, and also in illustrating and explaining the condition to a patient. It should be understood that the roller-ball 82 is given as an example of how to correlate the detected light to a particular location. Indeed, there may be many other ways to accomplish the same or similar functionality. For example, an optical device may be used to in a similar manner to indicate relative position.

Figure 6:
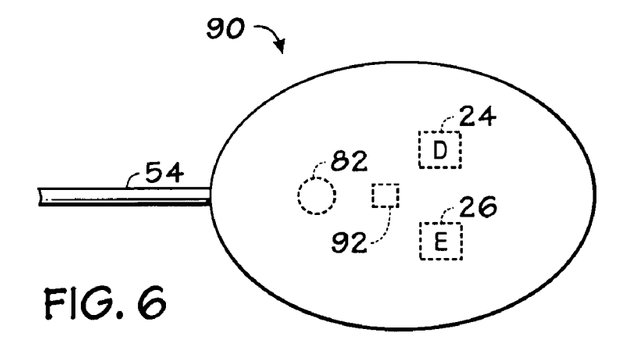
FIG. 6 illustrates a sensor having a thermometer sensor in accordance with yet another alternative embodiment of the present invention.

Additional features may be added to the above described sensor 80 in order to provide additional capability and to enhance performance. For example, FIG. 6 illustrates a sensor 90 having a roller-ball 82 and a temperature sensor 92 in accordance with an exemplary embodiment of the present invention. It may be desirable to measure the temperature of the patient's tissue because the radiation spectrum from the emitter 26 may change in accordance with the temperature. Specifically, as temperature increases, the water spectrum is blue-shifted. The temperature may be taken into account when calculating the various parameters by modifying coefficients used in the algorithms to account for any spectrum shifting. Additionally, the temperature measurement may help in distinguishing types of skin wounds. For example, temperature may help in distinguishing between an elevated water level due to an acute injury, which exhibits local temperature increase, and an elevated water level due to a chronic injury, which should not show an increase in temperature. Accordingly, the sensor 90 implementing the temperature sensor 92 may be more accurate and provide increased functionality than a sensor without a temperature sensor.

Figure 7:
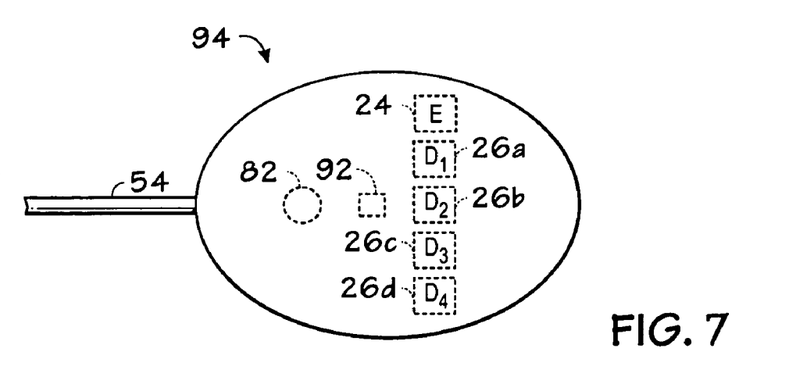
FIG. 7 illustrates a sensor having a roller-ball, a thermometer and multiple detectors in accordance with still another alternative embodiment of the present invention.

Another embodiment combines all of the above described features into a single sensor. FIG. 7 illustrates a sensor 94 that has multiple detectors 26a-d, a roller-ball 82, and a temperature sensor 92. The sensor 94 provides all of the advantages described earlier with respect to the embodiments illustrating the features separately. Alternative arrangements of the various features can also be envisioned, and the scope of this disclosure should not be limited to the exemplary embodiments described herein.

Figure 8:
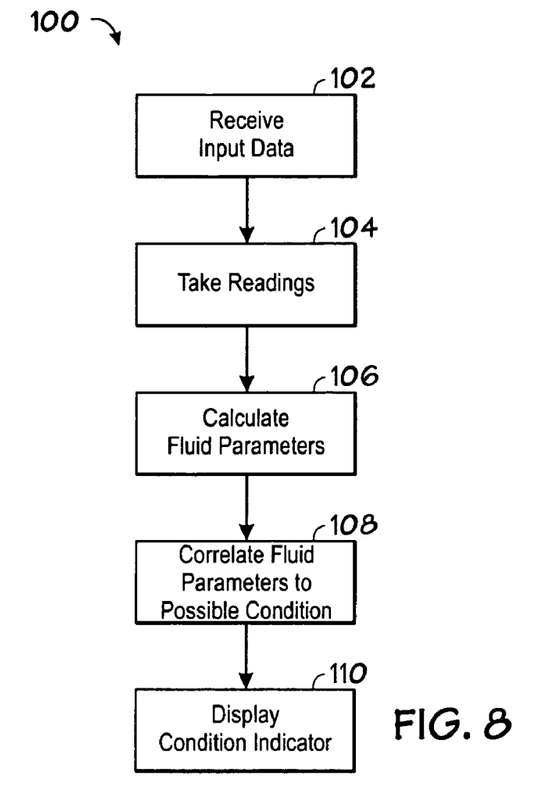
FIG. 8 illustrates a technique for detecting skin wounds and compartment syndromes in accordance with an exemplary embodiment of the present invention.

Turning to FIG. 8, a technique of detecting skin wounds and compartment syndromes in accordance with embodiments of the present invention is represented by a block diagram and generally designated by the reference numeral 100. Initially, data is input into a spectrophotometric device, as indicated at block 102. For example, information such as baseline fluid levels may be input, as they vary according to the particular organ or compartment of the body that is to be measured. Additionally, information such as the part of the body where measurements are to be taken may be input, as different compartments may require different sets of coefficients. For example, if the patient has been involved in an accident and the patient may be suffering from abdominal compartment syndrome, a clinician could enter data indicating that the abdominal compartment will be measured and the baseline fluid levels associated with that compartment will be used for the calculations. Alternatively, if the patient has been confined to a bed or chair and the patient may be likely to develop bed sores, a user could select baseline parameters associated with those particular pressure points, including historical parameters from the same patient, so that an appropriate correlation may be made.

After the baseline parameters have been selected or the data has been entered into the spectrophotometric device 20, readings may be taken of areas where the suspected condition may be developing, as indicated at block 104. The readings are made by placing the sensor on locations around a probable problem spot or by moving the sensor over an area of skin while taking measurements. For example, in the case of abdominal compartment syndrome, multiple points on the abdomen may be tested with the monitor. Alternatively, if the monitor is equipped to do so, an area may be continuously probed while moving the monitor across the patient's abdomen.

Figure 9:
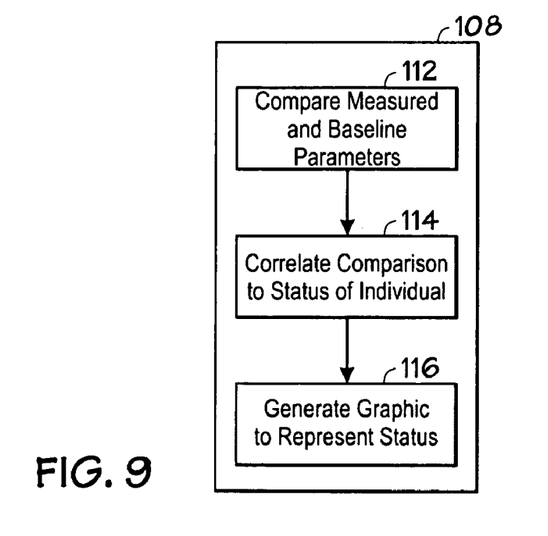
FIG. 9 illustrates a technique for correlating fluid parameters to a possible condition in accordance with an exemplary embodiment of the present invention.

Once obtained, the readings are used to calculate fluid parameters using algorithms programmed into the spectrophotometric device 20, as indicated at block 106. One fluid parameter that may be determined, for example, is the water percentage of the measured tissue. The calculated fluid parameter may be correlated to a possible condition status, as indicated at block 108. As shown in FIG. 9, the correlation may include several steps, which will be discussed in greater detail below. Essentially, the correlation may include a comparison with baseline parameters to determine the presence of a condition.

A condition indicator may be displayed representing the fluid measurements or the amount of deviation from baseline values, as indicated at block 110. The condition indicator may be a decimal number or a whole number indicating the percentage of water in the tissue, for example. In an alternative embodiment, a number correlating the amount of deviation from baseline values may be displayed. In yet another embodiment, a graphical representation of the area over which a sensor has passed is displayed. The graphical representation may be coded to indicate the water percentage or amount of deviation from the baseline parameters of a particular area. Specifically, the graphical representation may be color coded, as discussed above.

The correlation of the fluid parameters to a condition status of block 108 may include several discrete steps, as set forth in the block diagram of FIG. 9. For example, the measured parameters may be compared to baseline parameters, as indicated at block 112. The baseline parameters may be entered or stored in the monitor and used to determine whether or not measured parameters indicate a deviation from a normal state. A categorization may be performed based on the comparison of the measured parameters with the baseline parameters as indicated at block 114. For example, if the measured parameters are within an acceptable range of the baseline parameters, the patient's condition may be categorized as normal. As the measured parameters move further away from the baseline parameters, however, the patient's condition may be categorized as abnormal or severely abnormal, for example. The abnormal state may indicate a particular likelihood that a condition is developing, while a severely abnormal state may indicate that a particular condition is present.

After the measured parameters have been compared to the baseline parameters and the status of the condition has been determined, a graphic may be generated to represent the status, as indicated at block 116. As discussed above, the graphic may simply consist of a number indicative of the presence and severity of a potential condition. Alternatively, a particular monitor may be configured to display a graphical representation of an area over which a sensor has taken measurements. The graphical representation may be coded, such as with color, to indicate the status in a particular area.

The data or images generated and displayed according to the technique 100 may be interpreted by a clinician. Specifically, the clinician may interpret the displayed results in light of the patient's medical history to make an informed diagnosis. The technique 100 allows for non-invasive diagnosis of skin wounds and compartment syndromes at early stages, thus allowing the opportunity to provide proper care and to take measures to prevent the occurrence of further damage.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for determining fluid parameters of living tissue comprising:
    transmitting electromagnetic radiation at a tissue site using at least one emitter;

detecting the electromagnetic radiation reflected and scattered by living tissue beneath the tissue site using at least one photodetector, the photodetector generating a signal corresponding to the detected electromagnetic radiation;

processing the generated signal to calculate localized fluid parameters of the living tissue beneath the tissue site;

correlating the calculated fluid parameters to a condition status indicative of a localized accumulation of fluid in the living tissue and a potential skin wound by comparing the calculated fluid parameters with baseline fluid parameters specific to the living tissue and correlating the comparison to the condition status; and indicating the condition status on a display.

2. The method of claim 1, wherein calculating fluid parameters comprises calculating a ratio of water-to-lean mass.

3. The method of claim 1, wherein calculating fluid parameters comprises calculating a ratio of water-to-water, protein and fat.

4. The method of claim 1, wherein calculating fluid parameters comprises calculating a ratio of water-to-fat.

5. The method of claim 1, comprising transmitting electromagnetic radiation over an area of tissue.

6. The method of claim 1, wherein indicating condition status comprises displaying discrete values, wherein a first discrete value indicates normal status, second discrete value indicates abnormal status, and a third discrete value indicates severely abnormal status.

7. The method of claim 1, wherein the baseline parameters correspond to fluid parameters of layers of skin.

8. The method of claim 1, comprising generating and displaying a graphical representation of the condition status.

9. The method of claim 8, wherein the graphical representation is color coded to represent the condition status.

10. The method of claim 1, wherein the baseline fluid parameters comprises an earlier measurement of normal fluid content from the living tissue of a patient.

11. The method of claim 1, comprising processing the generated signal to calculate localized fluid parameters of a compartment beneath the tissue site, and correlating the calculated fluid parameters to a condition status indicative of a localized accumulation of fluid in the compartment and a potential compartment syndrome by comparing the calculated fluid parameters with baseline fluid parameters specific to the compartment and correlating the comparison to the condition status.

12. A system for detecting compartment syndromes comprising:
a sensor comprising at least one emitter and at least one detector;
a spectrophotometric unit communicatively coupled to the sensor and configured to calculate localized fluid parameters and correlate the localized fluid parameters to a condition status indicative of a localized accumulation of fluid in a compartment and compartment syndrome, wherein the spectrophotometric unit compares the calculated fluid parameters to baseline fluid parameters specific to the compartment and determines the condition status from the comparison; and
a display coupled to the spectrophotometric unit configured to display the condition status.

13. The system of claim 12, wherein the sensor comprises a location sensor, the location sensor being configured to indicate a position of the sensor relative to a start position.

14. The system of claim 13, wherein the location sensor comprises a button configured to indicate the start position of the sensor by actuation of the button.

15. The system of claim 13, wherein the location sensor is configured to indicate the start position of the sensor by a voice command.

16. The system of claim 13, wherein the location sensor is configured to indicate the start position of the sensor relative to a fixed point on a bed or operating table.

17. The system of claim 13, wherein the location sensor comprises a roller-ball sensor.

18. The system of claim 12, wherein the sensor comprises a thermometer, the thermometer configured to take temperature readings as the spectrophotometric unit calculates fluid parameters.

19. The system of claim 12, wherein the sensor comprises a roller-ball and a thermometer, wherein the roller-ball is configured to indicate a position of a sensor relative to a start position, the start position being determined by actuation of a button, and wherein the thermometer is configured to take temperature readings as the spectrophotometer unit calculates fluid parameters.

20. The system of claim 12, wherein the spectrophotometric unit is coupled to the sensor via a cable.

21. The system of claim 12, wherein the sensor communicates with the spectrophotometric unit wirelessly.

22. The system of claim 12, wherein at least one detector comprises multiple detectors positioned at varying distances from the at least one emitter.

23. The system of claim 12, wherein the at least one emitter comprises multiple emitters positioned at varying distances from the at least one detector.

24. The system of claim 12, wherein the baseline fluid parameters comprises an earlier measurement of normal fluid content of a patient.

25. The system of claim 12, wherein the at least one detector and the at least one emitter are disposed between 1 to 5 mm apart.

26. The system of claim 12, wherein the at least one detector and the at least one emitter are disposed between 5 to 15 mm apart.

27. The system of claim 12, wherein the spectrophotometric unit is configured to calculate localized fluid parameters and correlate the localized fluid parameters to a condition status indicative of a localized accumulation of fluid in living tissue and a potential skin wound, wherein the spectrophotometric unit compares the calculated fluid parameters to baseline fluid parameters specific to the living tissue and determines the condition status from the comparison.

28. A method for diagnosing skin wounds and compartment syndromes comprising:
selecting a baseline fluid parameter specific to a living tissue or compartment beneath a tissue site in a spectrophotometric device;
using the spectrophotometric device to calculate data indicative of a potential skin wound or compartment syndrome, comprising placing a sensor on an area of a patient's skin over the tissue site for which baseline fluid parameters were entered and taking localized measurements using the sensor, the spectrophotometric device being configured to display the localized measurements; and
making a diagnosis of the potential skin wound or compartment syndrome based on consideration of the patient's medical history and the data calculated by the spectrophotometric monitor.

29. The method of claim 28, wherein entering baseline fluid parameters comprises entering fluid parameters corresponding to a normal tissue fluid content of the living tissue or compartment to be measured by the spectrophotometric monitor.

30. The method of claim 29, wherein said normal fluid content comprises earlier measurements from the tissue site on the patient.

31. The method of claim 28, wherein using a spectrophotometric monitor comprises moving a sensor across an area of the patient's skin.

* * * * *